United States Patent [19]
Lawton

[11] Patent Number: 5,365,023
[45] Date of Patent: Nov. 15, 1994

[54] ELASTOMERIC STETHOSCOPE COVER

[76] Inventor: Gary P. Lawton, 13 Sagamore Cove, Branford, Conn. 06405

[21] Appl. No.: 62,420

[22] Filed: May 13, 1993

[51] Int. Cl.⁵ .......................... A61B 7/02; A61B 5/02; A61B 7/04
[52] U.S. Cl. .................... 181/131; 128/715; 381/67
[58] Field of Search .............. 181/131, 132; 381/67; 128/715, 773, 798, 639

[56] References Cited

U.S. PATENT DOCUMENTS

| | | | |
|---|---|---|---|
| 2,651,380 | 9/1953 | Brandenburg | 181/131 |
| 3,255,841 | 6/1966 | Hasbrouck | 181/131 |
| 4,401,125 | 8/1983 | Taylor et al. | 181/131 X |
| 4,461,368 | 7/1984 | Plourde | 181/131 |
| 4,871,046 | 10/1989 | Turner | 181/131 |

*Primary Examiner*—Khanh Dang
*Attorney, Agent, or Firm*—Cesari and McKenna

[57] ABSTRACT

An elastic, disposable cover for the head of a stethoscope. The disk-shaped cover is manufactured from latex or other material that is sufficiently elastomeric to allow the cover to be stretched over the stethoscope head during installation, and yet snap back to remain taut after installation and during use of the stethoscope. The outer edge of the disk is preferably rolled, and the disk is preferably pre-shaped in a shallow parabola, to further ease installation and removal. Since the cover may be fit to a wide variety of stethoscope head types, it is much more practical and easier to use than prior stethoscope covers.

4 Claims, 3 Drawing Sheets

ELASTOMERIC STETHOSCOPE COVER

FIELD OF THE INVENTION

This invention relates to an elastic, disposable cover for the head of a stethoscope, which helps to prevent the spread of infectious disease.

BACKGROUND OF THE INVENTION

Acquired infections are an unfortunate fact of hospital stays. It is not uncommon for an infectious organism to spread throughout an entire section of a hospital, particularly within an intensive care unit. Every once in a while, a particularly troublesome organism will affect an entire hospital, and eradication of the organism requires the use of multiple, expensive and toxic antibiotics. Such epidemics cost the hospital, the patient, and insurance companies untold amounts in direct costs, add to the patient's length of stay, and increase morbidity and mortality.

As a result, absolutely every health care worker is encouraged, expected, and required by the hospital as well as the Occupational Safety and Health Administration (OSHA) to wear gloves when they come into contact with patients. Many hospitals now conduct mandatory "universal precautions" courses for all employees that come into contact with patients, prompted by continuing concern with the acquired immune deficiency syndrome virus. These courses, typically repeated on a regular basis, teach that every situation where a patient is to be examined must be considered for the spread of infection. For example, all instruments used to examine patients must either be disposable (such as otoscopicspecula, tongue blades, cotton swabs, and thermometers), or be sterilizable between uses.

It is thus considered unprofessional, irresponsible, and a violation of universal precautions for a health care worker to not wear gloves when examining patients or to neglect to wash hands thoroughly between patients. In such an environment, gloves in various sizes and antiseptic hand cleaners are conspicuously located on cabinets, shelves, and racks, everywhere in sight.

However, the use of certain instruments by hospital personnel must also play a role in hospital-acquired epidemics. Consider, for example, a respiratory intensive case unit. Respiratory patients, who are typically at an increased risk of developing pneumonia, usually have foreign objects inserted into their bodies such as breathing tubes. Respiratory therapists and nurses use stethoscopes every time they visit each and every patient. The stethoscope may become contaminated while examining the lungs of an infected patient, and the therapist then uses the inadequately clean stethoscope on the next patient. Even if the therapist were to clean his stethoscope and hands, certain microbes known to cause pneumonia are resistant to the most commonly used antibiotics, and contaminants may remain in hard-to-clean crevices. As a result, even the most careful of therapists will unavoidably transfer infections from one patient to the next.

In an emergency room, the situation is similar. All care-givers use a stethoscope, placing it on the chest and back of almost every single patient they encounter. Sometimes the stethoscope is put to the groin or the abdomen to listen for other sounds.

But emergency room patients often have slimy, sweaty skin, and may be unshowered or totally unkempt after being rushed into the hospital. In the worst scenario, trauma room patients arrive in the emergency room covered in blood, HIV-status unknown. As a result, accepted and often mandatory precautions for the arrival of a new patient include donning of goggles, mask, plastic coverall gown, shoe covers, and of course, gloves.

When the patient arrives, the physician always performs the potential life-saving step of applying a stethoscope to listen to the patient's chest immediately, without regard to whatever fluids may cover the chest. The stethoscope is then thrown around the neck, until it is used again on the next patient. The stethoscope is rarely, if ever, cleaned between patients. The bloodied stethoscope may also be stored in the pocket of the physician's white lab coat, where it comes into contact with other items in the pockets. In a large city hospital, this scenario may be repeated many times in a single evening.

In neglecting the role of the stethoscope in the practice of universal precautions, a significant threat to the health and lives of health care workers and patients alike as been permitted to continue. Patients, doctors, hospitals and regulatory agencies have just not adequately considered the stethoscope and the potentially huge health risk it represents.

That is not to say, however, that certain people have not recognized the potential for the spread of infection via the stethoscope.

For example, U.S. Pat. No. 4,461,368 issued to Plourde on Jul. 24, 1984 discusses the problem generally. That patent proposes the use of a sterile diaphragm cover consisting of a membrane sheet mounted on a rigid rim member. The rigid rim member contains one or more tabs adapted to be engaged over the outer edge of the stethoscope.

Devices such as that shown in the Plourde patent are not in widespread use, however, probably for several reasons. First, the covers must be custom-made for each individual type of stethoscope. Since stethoscope heads tend to be of different designs, and since the selection of a particular stethoscope depends upon the application to which it is put, as well as a matter of the physician's or nurse's personal preference, many different versions of a Plourde-type cover would have to be kept in inventory in a typical hospital. It is probably not practical nor realistic to expect a hospital to stock custom covers for each type of stethoscope head.

Furthermore, an emergency room physician is unlikely to have the time to search for a cover which fits his particular type of stethoscope. And, even if the physician could quickly find the correct type of cover, the installation of such a cover onto the stethoscope would appear to be unnecessarily cumbersome, since a pair of tabs must be aligned with a corresponding portion of a stethoscope ring.

U.S. Pat. 4,871,046 issued to Turner also discusses a type of stethoscope cover. This cover is formed from a type of loose-fitting, plastic bag which may be easily dispensed from a roll. However, covers such as this one are also not in widespread use, probably for several reasons.

First, the corners of the bag are prone to fold over, and the sides of bag itself are prone to wrinkle during application to the skin. These folded or wrinkled sections of bag material interfere with the accuracy and level of sound transmitted to the stethoscope.

Second, the bag only provides a loose fit around the stethoscope head. The loose fit, in turn, means that infectious contaminants may still find their way onto the stethoscope, via the openings left by the loose fitting bag. The potential for transmission of disease has thus not been eliminated if the stethoscope is subsequently used in the unprotected state before being cleaned again.

What is needed is a disposable, clean stethoscope cover which can be used with a wide variety of stethoscope types. It should not provide any path for infectious disease to reach the stethoscope head.

The cover should be easy to install and remove from the stethoscope, to encourage its widespread use.

It should also be designed to avoid interference with sound transmission during its use.

SUMMARY OF THE INVENTION

It is an object of this invention to help prevent the spread of infectious disease via stethoscopes in a typical hospital environment.

The invention is a stethoscope head diaphragm cover formed exclusively from a disk of suitably elastic material such as latex. The cover is pre-formed in the same general shape as a stethoscope head, with the outer diameter of the latex cover in its relaxed state being smaller than that the diameters of common stethoscopes. The cover thus fits the stethoscope head snugly after being installed, regardless of the particular geometry of the stethoscope head.

The elastic material is selected to be thin enough to avoid muffling the sounds through the stethoscope diaphragm, while being thick enough to prevent violation organisms or fluids, and thick enough to prevent breakage during installation.

In the preferred embodiment, the cover also preferably has a rolled edge formed in the same manner as a common prophylactic. The rolled edge greatly assists with installation and removal of the cover.

The cover provides a tight fit around all of the surfaces of the stethoscope typically coming in contact with a patient. This prevents transmission of fluids containing potentially infectious organisms to even the peripheral surfaces of the stethoscope.

The tight-fitting cover also does not interfere in any way with the transmission of sound to the stethoscope diaphragm.

It is easy to install and remove from the stethoscope, and disposable and inexpensive to manufacture. It may be made to a universal size which fits all of the various stethoscopes now in use.

BRIEF DESCRIPTION OF THE DRAWINGS

The novel features believed to be characteristic of the invention are pointed out in the appended claims. The best mode for carrying out the invention and its particular features and advantages can be better understood by referring to the following detailed description, when read together with the accompanying drawings, in which:

DETAILED DESCRIPTION OF A PREFERRED EMBODIMENT

Figure 1:
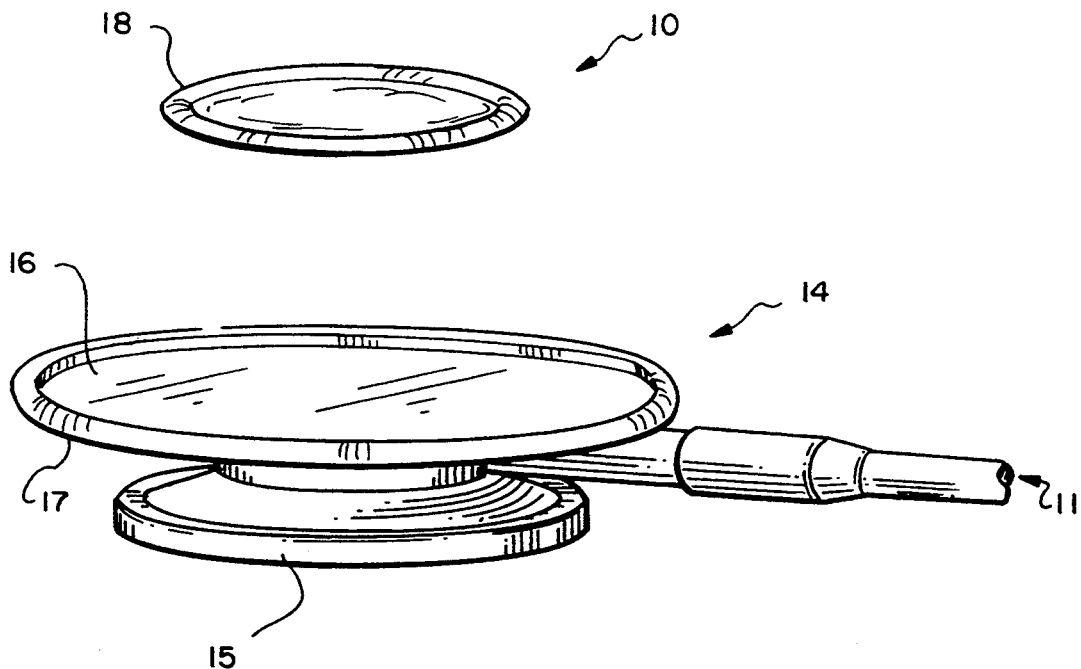
FIG. 1 is a perspective view of a disposable elastic diaphragm cover, according to the invention, being used with a Littman-type stethoscope head.

FIG. 1 shows a disposable stethoscope cover 10 in accordance with the invention. The cover 10 is illustrated in this view as being used with a particular type of stethoscope 11 known as a Littman stethoscope, but the cover 10 may also be used with other types of stethoscopes.

A short explanation of the various parts of a common stethoscope assists understanding how the inventive cover 10 is constructed and how it operates. A typical Littman stethoscope 11 includes a "combination" type of acoustical pick-up 12. This type of pick-up 12 includes a central body 13 having both a diaphragm end 14 and a bell end 15; other types of stethoscope pick-ups 12 include only a diaphragm 14 or a bell 15, as will be described below.

As is well known, the bell 15 includes an open cavity (hidden in the view of FIG. 1) which extends outwardly from the body 13. Nearby sounds resonate in the cavity and are passed through the body 13 to a tube 16, which in turn passes sounds to the user's ear.

The diaphragm 14 is also a formed as a cavity, but typically having a somewhat shallower depth than the depth of the cavity of the bell 15. The diaphragm 14 cavity has a flat external surface formed thereon. This surface is typically formed of a semi-rigid plastic disk 17 held in place by a peripheral holding ring 18 encompassing the outer circumference of the cavity.

The diaphragm 14 is most commonly used to listen to high-pitched sounds of the heart and lung, while the bell 15 is used to listen to low rumbles of the heart. Only cardiologists routinely use the bell 15, and thus most health professionals are not skilled enough to fully utilize both types of pick-ups 12. As a result, the most commonly used part of a Littman stethoscope is the diaphragm 14.

According to the invention, the cover 10 is formed from a generally disk-shaped piece of latex or some other appropriate elastomeric material. The cover 10 includes both a central portion 19 and a rolled peripheral edge 20.

The material used to form the cover 10 is any suitable elastomer which can be made sterile, or at least clean. The latex material used in manufacturing common surgical gloves has been found to be most satisfactory. One example of such a material is the latex used by Ansell Incorporated, of Dotham, Ala. for manufacturing surgical gloves distributed by VHA Supply Company, of 320 Oecker Drive, Irving, Tex. A relatively thin material is the best to use, as it minimizes, distortion in the sounds transmitted to the stethoscope 11.

The central portion 19 of the elastomeric material is pre-formed in cross-section in the general shape of a parabola, similar in shape to the external shape of the end of typical stethoscope pick-up such as the diaphragm 14 or bell 15. However, the cover has a smaller diameter than most common diaphragms 14 or bells 15.

The rolled edge 20 is preferably formed as an integral part of the cover 10 in much the same manner as the rolled edge formed on a common prophylactic. The rolled edge 20 assists with installation and removal of the cover 10, as well as with insuring that contaminants do not reach the surface of the stethoscope 11.

In the relaxed state, before being installed on the stethoscope 11 as shown in FIG. 1, the cover 10 is thus generally shaped as a shallow surface, approximately parabolic in cross-section having a rolled edge 20, with the outer diameter of the rolled edge 20 being smaller than the diameter of either the diaphragm 14 or the bell 15.

Figure 2:
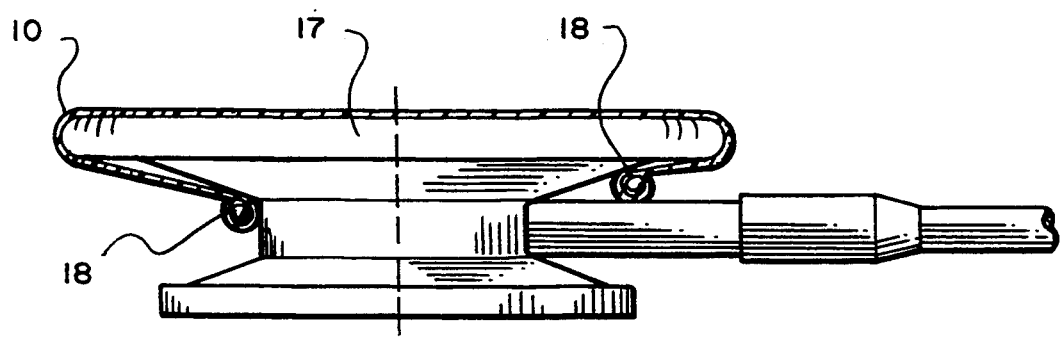
FIG. 2 is a cross-sectional view of the cover after it has been installed over the diaphragm of the stethoscope shown in FIG. 1.

FIG. 2 shows the cover 10 after it has been installed on the stethoscope 11. To install the cover 10, the cover 10 is typically first positioned such that a portion of the rolled edge is placed underneath the ring 18. The rolled edge 20 is then pulled across the top of the diaphragm 14 cavity and plastic disk 17, temporarily stretching the cover 10 to a diameter larger that the diameter of the ring 18. The central portion 19 of the cover 10 is then secured over the diaphragm 14 by simply releasing hold of the rolled edge 20.

Because the cover 10 is made from an elastic material, upon being released it snaps back to conform to the external shape of the diaphragm 14. In fact, once the cover 10 is installed on the stethoscope 11, it encompasses nearly all of the external surface of the head of the stethoscope 11 to which it has been applied.

As shown, the rolled edge 20 snaps back to snugly fit against the outer diameter of the central body 13. Depending upon the design of the diaphragm 14, in the area of the tube 16, the rolled edge may be prevented from fitting snugly against the outer diameter of the central body 13. However, the rolled edge does fit snugly against the outer diameter of the tube 16 and/or other outer surfaces of the diaphragm 14.

Figure 3:
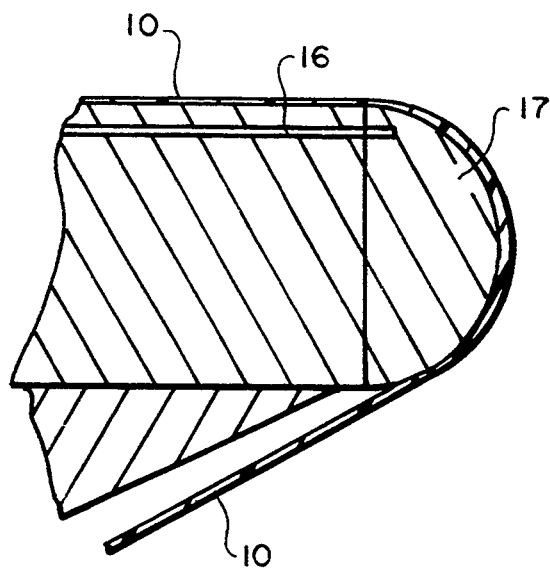
FIG. 3 is a cross-sectional, close-up view of the elastic cover and the manner in which its rolled edge is stretched about the stethoscope body to prevent infectious organisms from reaching the stethoscope.

The close-up cross sectional view of FIG. 3 shows the rolled edge in detail. The central portion 19 is typically fit snugly against the outer surface 21 of the parabolic cavity forming the diaphragm 14. The rolled edge 20 typically settles in a niche 22 formed at the intersection of the lower portion of the diaphragm 14 and the upper portion of the body 13. As a result, any contaminants travelling generally in the direction of the arrow A are prevented from reaching any portion of the stethoscope 11 generally above the dashed line B which will come in contact with the patient. The rolled edge 20 will also protect the stethoscope 11 below the dashed line B from contaminants travelling along the direction of the arrow C.

Figure 4:
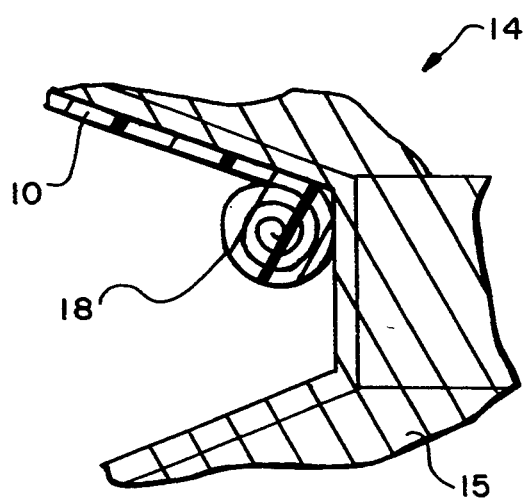
FIG. 4 is another partial, cross-sectional, close-up view of the elastic cover after installation.

FIG. 4 is a close-up view of such portions of the stethoscope 11 which lie above the line B of FIG. 3. The central portion 19 of the cover 10 stretches tightly against the outer periphery of the diaphragm 14, the ring 18, and outer surface 21.

It has been found that the cover 10 does not interfere with the acoustics the diaphragm in any significant way. This is because the cover 10 is stretched taut across the upper portion of cavity 23 of the diaphragm 14, and once in the stretched state, the cover 10 is typically of an even smaller thickness than the plastic cover 17 which, of course, also does not interfere with acoustic transmission.

Figure 5:
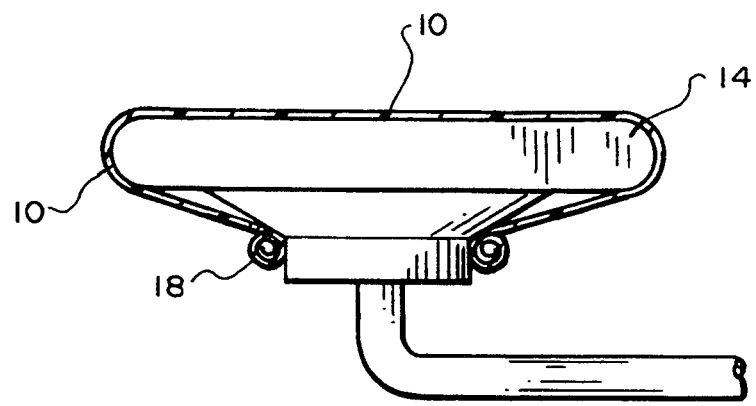
FIGS. 5 and 6 are cross-sectional views of the elastic cover fitted to two other types of stethoscopes which consist of diaphragms only.

FIG. 5 shows the cover 10 installed on a stethoscope 11 having a diaphragm 14 pick-up only. With this type of stethoscope, the tube 16 is typically position in the bottom center of the body 13, and the cover 10 fits snugly around the entire outer circumference of the body 13.

Figure 6:
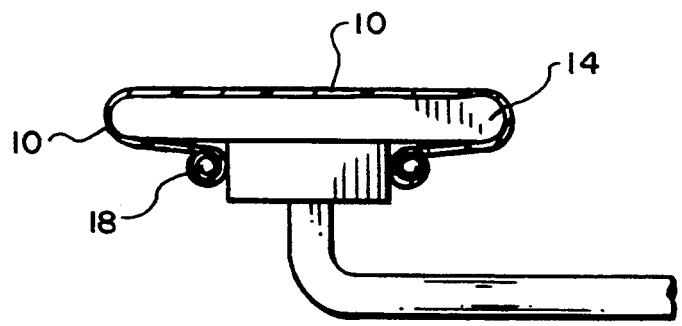

FIG. 6 is a similar view showing the that cover likewise snugly fits a stethoscope having a diaphragm which is enclosed within the body 13.

The terms and expressions which have been employed above are used as terms of description and not meant to be limiting in any way, and there is no intention to exclude any equivalents of the features shown and described or portions thereof, and it should be recognized that various modifications are possible while remaining within the scope of the invention as claimed.

What is claimed is:

1. An elastic cover for a stethoscope head, the stethoscope head consisting of a cavity extending outwardly from a central body, the cavity terminating in an outer rim, the rim having an exterior surface that tapers outwardly from the central body, the cover being formed from a disk of elastomeric material, the cover having a central portion and a spiral-rolled peripheral edge, the maximum outer diameter of the central portion in its relaxed state being smaller than the diameter of the rim, and the elastomeric material being sufficiently elastic such that the central portion snugly fits the stethoscope head along the rim and the spiral-rolled peripheral edge snugly fits the exterior surface of the cavity after installation of the cover on the stethoscope head.

2. In combination:
 a stethoscope having a base portion, and a diaphragm cavity portion in the form of a shallow surface, approximately parabolic in cross-section, the diaphragm cavity being disposed adjacent the base portion, and the diaphragm cavity having an exterior tapering surface; and
 a stethoscope cover formed of a continuous and flexible sheet of elastomer, the cover having a central portion and a spiral-rolled peripheral edge, the cover being sized and the elastomer being sufficiently elastic such that the central portion of the cover stretches across the diaphragm cavity of the stethoscope and the spiral-rolled edge fits snugly against the exterior tapering surface of the diaphragm cavity.

3. A removable and disposable cover for a stethoscope which includes a stethoscope body having an acoustical cavity that is approximately parabolic in cross-section, the cavity having an outer opening at the periphery of the body, and the stethoscope also including a tube for carrying acoustic energy away from the cavity towards the ear of the user of the stethoscope, the said removable and disposable cover comprising a unitary piece of non-rigid elastomeric material, the cover also having a central portion and an annular spiral-rolled peripheral edge, the maximum diameter of the removable and disposable cover being less than the largest outer diameter of the outer opening of the parabolic cavity before the cover is installed on the stethoscope, and the elastomeric material is sufficiently elastic such that after the cover is installed on the stethoscope, the central portion of the cover is stretched across the outer opening and the spiral-rolled peripheral edge is positioned against the outer periphery of the stethoscope body, thereby preventing fluids and other extraneous matter that may be present on the skin of the patient from contacting any portion of the stethoscope coming in contact with the patient.

4. A removable and disposable cover as in claim 3 wherein the elastomeric material is sterile when manufactured.

* * * * *